United States Patent
Chakfe et al.

(10) Patent No.: US 10,617,542 B2
(45) Date of Patent: Apr. 14, 2020

(54) ELASTIC RING AND ASSOCIATED TREATMENT DEVICE FOR IMPLANTING IN A CONDUIT FOR CIRCULATION OF A BODY FLUID

(71) Applicants: ID Nest Medical, Strasbourg (FR); UNIVERSITÉ DE STRASBOURG, Strasbourg (FR)

(72) Inventors: Nabil Chakfe, Hindisheim (FR); David Contassot, Strasbourg (FR)

(73) Assignees: ID Nest Medical, Strasbourg (FR); UNIVERSITE DE STRASBOURG, Strasbourg (FR)

( * ) Notice: Subject to any disclaimer, the term of this patent is extended or adjusted under 35 U.S.C. 154(b) by 0 days.

(21) Appl. No.: 15/763,361

(22) PCT Filed: Oct. 26, 2016

(86) PCT No.: PCT/EP2016/075786
§ 371 (c)(1),
(2) Date: Mar. 26, 2018

(87) PCT Pub. No.: WO2017/072168
PCT Pub. Date: May 4, 2017

(65) Prior Publication Data
US 2018/0296374 A1    Oct. 18, 2018

(30) Foreign Application Priority Data
Oct. 26, 2015  (FR) ..................................... 15 60187

(51) Int. Cl.
*A61F 2/90* (2013.01)
*A61F 2/856* (2013.01)
*A61F 2/06* (2013.01)

(52) U.S. Cl.
CPC ................. *A61F 2/90* (2013.01); *A61F 2/06* (2013.01); *A61F 2/856* (2013.01);
(Continued)

(58) Field of Classification Search
CPC ............... A61F 2002/061; A61F 2/064; A61F 2002/821; A61F 2/856; A61F 2/90
See application file for complete search history.

(56) References Cited

U.S. PATENT DOCUMENTS

| | | | |
|---|---|---|---|
| 8,277,501 B2 * | 10/2012 | Chalekian | ............... A61F 2/856 623/1.15 |
| 2003/0120292 A1 * | 6/2003 | Park | ..................... A61B 17/083 606/153 |

(Continued)

FOREIGN PATENT DOCUMENTS

| | | |
|---|---|---|
| EP | 2749252 A1 | 7/2014 |
| EP | 2895110 A1 | 7/2015 |

(Continued)

OTHER PUBLICATIONS

International Search Report issued in PCT Patent Application No. PCT/EP2016/075786 dated Nov. 28, 2018.

*Primary Examiner* — Suba Ganesan
(74) *Attorney, Agent, or Firm* — Marshall, Gerstein & Borun LLP

(57) ABSTRACT

An elastic ring, defining an inner opening, an outer contour and an annular bearing surface between the inner opening and the outer contour. The ring is deformable between a rest position and an insertion position in which the inner opening has a diameter greater than its diameter in the rest position. The ring is also elastically biased towards the rest position. The ring includes at least three strands passing through the ring, each strand having a first end and a second end positioned on the outer contour, the inner contour of the (Continued)

opening being defined by a portion of each strand and having a pseudo-polygonal shape.

20 Claims, 3 Drawing Sheets

(52) U.S. Cl.
CPC ... *A61F 2002/061* (2013.01); *A61F 2002/067* (2013.01); *A61F 2210/0014* (2013.01); *A61F 2210/0057* (2013.01); *A61F 2220/0025* (2013.01); *A61F 2230/0052* (2013.01); *A61F 2250/0098* (2013.01)

(56) References Cited

U.S. PATENT DOCUMENTS

| | | |
|---|---|---|
| 2007/0112419 A1* | 5/2007 | Yadin ................ A61F 2/856 623/1.35 |
| 2007/0225750 A1 | 9/2007 | Ren et al. |
| 2008/0228256 A1* | 9/2008 | Erickson ............ A61F 2/064 623/1.11 |
| 2011/0034986 A1 | 2/2011 | Chou et al. |
| 2011/0257723 A1* | 10/2011 | McNamara ......... A61F 2/2412 623/1.11 |

FOREIGN PATENT DOCUMENTS

| WO | WO-2005/034810 A1 | 4/2005 |
|---|---|---|
| WO | WO-2014/041028 A1 | 3/2014 |

* cited by examiner

ELASTIC RING AND ASSOCIATED TREATMENT DEVICE FOR IMPLANTING IN A CONDUIT FOR CIRCULATION OF A BODY FLUID

TECHNICAL FIELD

The present disclosure relates to devices for implantation in a blood circulation conduit to treat areas having defects or diseases, such as dissecting aneurysms, occlusive lesions or compressions.

BACKGROUND

Document EP 2,895,110 describes a treatment device comprising a first implant and a second implant.

Such a device is generally implanted in a blood circulation conduit to treat areas having defects or diseases, such as dissecting aneurysms, occlusive lesions or compressions.

Endoluminal techniques are currently preferred for implanting the device, when they are practicable. Indeed, these techniques are less invasive for the patient and reduce the mortality and morbidity rates, as well as hospital stay durations.

Endoluminal techniques yield excellent results to treat lesions of the descending thoracic aorta, which is linear. However, in the case of the aortic arch, the implantation of the device using the endoluminal route poses some number of difficulties.

First, the first implant must be flexible enough to be able to adapt to the twists of the arterial shaft and to curve so that it can be satisfactorily brought into the aortic arch, then deployed while conforming to the anatomy of this vessel.

Next, several secondary implants must be mounted transversely through apertures arranged in the first implant. These secondary implants serve to fix the first implant axially for avoiding the risk of migration, and to cover the supra-aortic arterial branches in order to provide for revascularization of these branches.

To deploy a treatment device as cited above in a blood circulation conduit having a branch, it is known to first release the first implant into the blood flow conduit. An aperture arranged in the first implant is positioned facing the origin of each branch in which a second implant must be implanted. Then, the second implant is inserted into the aperture of the first implant through the branch. There are two insertion directions of the second implant into the aperture of the first implant, during placement of the treatment device. The second implant is either positioned in the aperture of the first implant while coming from the aperture of the first implant, or positioned in the aperture of the first implant while going toward the aperture of the first implant.

The second implant is next deployed and is fixed on the first implant via a retaining member that is for example a flange radially deployable at one end of the second implant.

To ensure proper working of the device once it is implanted in the body, it is necessary to produce a nearly complete seal between the inner contour of the aperture arranged in the first implant and the outer contour of the second implant.

This seal must be maintained all throughout the presence of the prosthesis in the patient, in particular when movements of the first implant and/or secondary implants occur.

Document WO 2005/034810 describes a prosthesis comprising an aperture and a deformable ring of the aforementioned type, positioned around the aperture, to keep a secondary implant in position relative to a primary implant in a treatment device. The deformability of the ring around 4% limits the effect of the elastic return of the steel secondary implant after it has been implanted. Such a ring nevertheless has a very limited deformability. In particular, the annular helical spring providing the elasticity of the ring is kept very rigidly in a bent edge of the opening, which greatly limits the deformability. The seal of the device is therefore not always perfect, in particular if the secondary implant moves, and/or is not aligned correctly with an axis perpendicular to the opening.

SUMMARY OF THE DISCLOSURE

The present disclosure relates to an elastic ring defining an inner opening, an outer contour and an annular bearing surface between the inner opening and the outer contour, the ring being deformable between a rest position and an insertion position, in which the inner opening has a diameter greater than its diameter in the rest position, the ring being elastically biased towards the rest position.

The disclosure further relates to a treatment device comprising such an elastic ring positioned in an aperture, on the body of an implant. Such a treatment device is intended to be implanted in a cavity of a living being. The cavity is a region of a circulatory network for a body fluid comprising at least one conduit for circulation of a body fluid, such as a blood circulation conduit. Furthermore, the network for example comprises a branch protruding transversely from the first conduit. For example, in the region of the cavity, the network has collateral branches to the circulation conduit. In one example, the blood circulation conduit is the aorta, in which a first implant is implanted. A second implant is deployed in an artery connected on the aorta, such as the iliac artery, the renal artery, the superior mesenteric artery, the celiac arterial trunk and the supra-aortic arterial trunks, etc.

Alternatively, the first implant is intended to be positioned in the aortic arch. The second implant is then placed in one of the branches emerging in the aortic arch, such as the left common carotid artery, the left subclavian artery or the brachiocephalic arterial trunk. Other applications are possible in the venous system, in particular in the inferior vena cava at the iliac bifurcation, at the joint of the renal veins and the superior vena cava, at the joint of its collateral branches.

However, to ensure proper working of the treatment device once it is implanted in the body, it is important to improve the seal of such a device.

One aim of the described embodiments is to provide an elastic ring making it possible to provide, simply and robustly, a very satisfactory seal of the treatment device throughout the entire time it is implanted in the patient.

To that end, the contemplated embodiments relate to an elastic ring of the aforementioned type, characterized in that the ring comprises at least three strands passing through the ring, each strand comprising a first end and a second end positioned on the outer contour, the contour of the inner opening being defined by a portion of each strand and having a pseudo-polygonal shape.

The elastic ring may comprise one or more of the following features, considered alone or according to all technically possible combinations:
 the strands are formed from a single wire, preferably braided;
 the strands extend substantially in a single plane;
 the width of the bearing surface is comprised between 30% and 60% of the diameter of the inner opening in the rest position;

the elastic ring comprises at least one pair of strands comprising two paired strands, the paired strands being strands connected to one another both by their first end and by their second end;

the paired strands define an oblong shape, in particular an eye shape;

the ends of the pairs of strands are distributed on the outer contour;

the elastic ring comprises an even number of strands, the strands being paired two by two, the ring preferably comprising eight strands;

the deformation of the ring is an elastic deformation allowing a reversible increase of at least 20%, advantageously of at least 30% of the diameter of the inner opening;

each strand has a diameter comprised between 0.1 mm and 2 mm, and preferably of 0.2 mm.

The described embodiments also relate to a treatment device comprising:

a first implant comprising a body, preferably tubular, defining an aperture, an elastic ring as previously described, the ring being positioned on the body of the first implant in the aperture, the inner opening defining the insertion passage of a second implant.

The treatment device may comprise one or more of the following features, considered alone or according to all technically possible combinations:

the body of the first implant is tubular;

the body is made up of a mesh of at least one wire, the ring being formed on the body of the first implant in the aperture using at least one wire of the mesh;

the ring is attached on the body of the first implant in the aperture;

the aperture is positioned on the wall of the body;

the aperture is positioned in the axis of the body.

BRIEF DESCRIPTION OF THE DRAWINGS

The described embodiments will be better understood upon reading the following description, given solely as an example, and made with reference to the accompanying figures, wherein.

DETAILED DESCRIPTION

A first treatment device 10 is illustrated by FIGS. 1 to 4. The first treatment device 10 is intended to be implanted in an inner cavity defined in the body of a human or animal.

Figure 2:
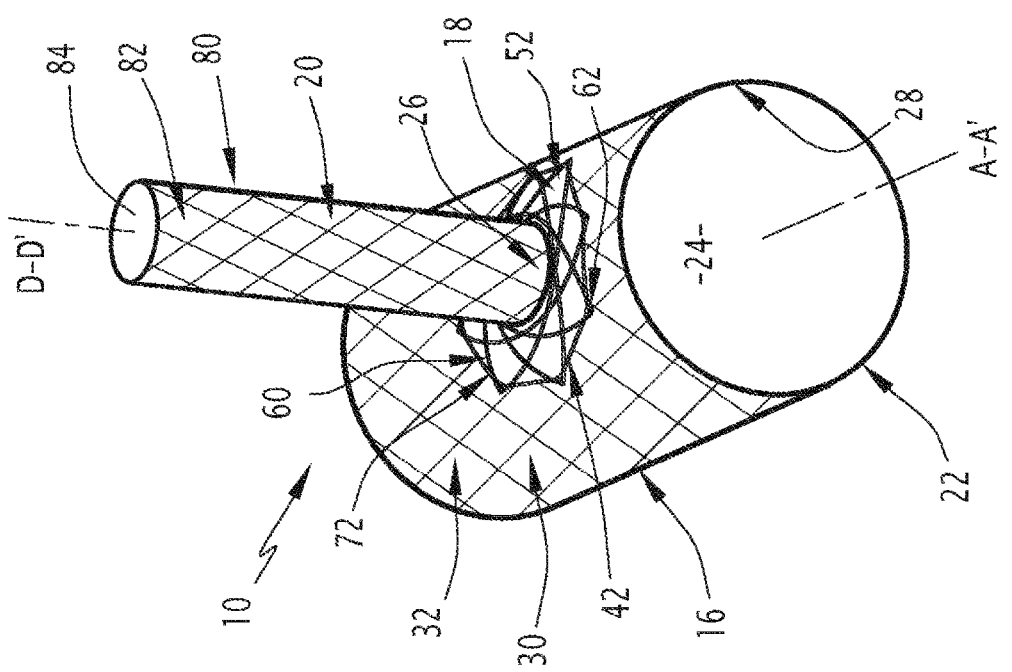
FIG. 2 is a sectional view according to a transverse plane of the device of FIG. 1.

In reference to FIG. 2, the cavity comprises a tubular primary segment 12 and a branch 14 connected to the primary segment 12.

The primary segment 12 and the branch 14 are for example blood circulation conduits in the vascular system of a human or animal being. The primary segment 12 is for example an artery or a vein, and the branch 14 is a blood circulation conduit connected to the artery or the vein.

In particular, the segment 12 can be the aorta, in particular at the aortic arch, or a linear segment of the aorta in which abdominal endoprostheses segments are connected.

The first treatment device 10 comprises a first implant 16 and an elastic ring 18.

Figure 1:
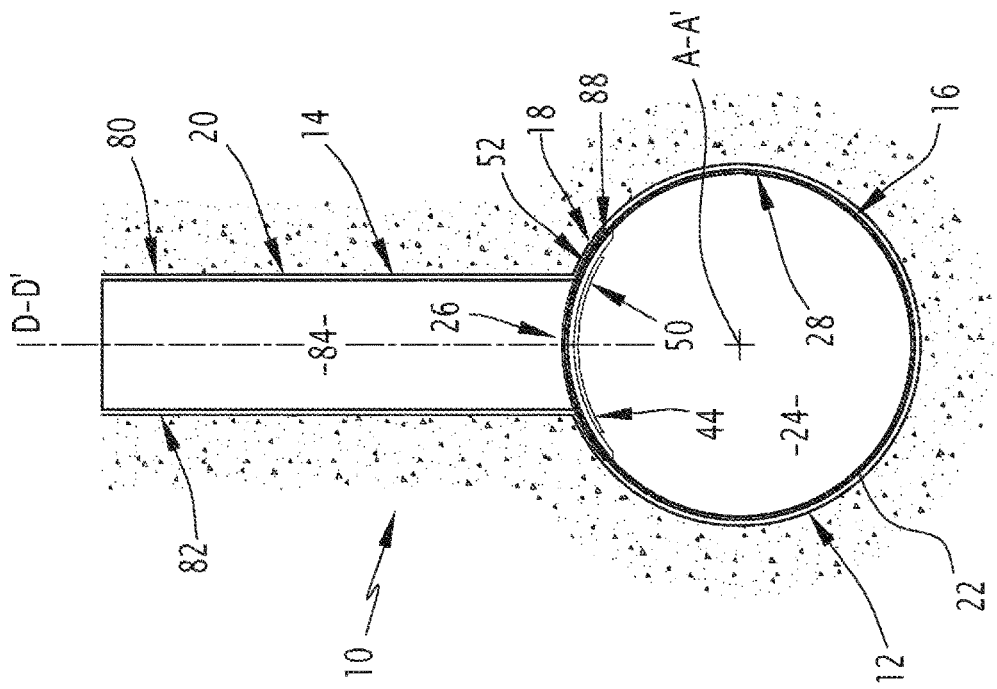
FIG. 1 is a three-quarters front perspective view of a first treatment device, in which a second implant has been mounted in the first implant.

Furthermore, as illustrated in FIGS. 1 and 2, the first treatment device 10 comprises at least one second implant 20 intended to be assembled transversely on the first implant 16 to protrude from the first implant 16 in the branch 14. In the first treatment device 10, the elastic ring 18 makes it possible to produce a seal around the second implant 20.

The first implant 16 is intended to be implanted in the primary segment 12. The first implant 16 comprises a first tubular body 22 defining a central passage 24 for circulation of a body fluid and an aperture 26 opening into the central passage 24.

The tubular body 22 has a tubular shape around a central primary axis A-A'. It comprises a tubular peripheral wall 28 advantageously formed by an open-cell frame 30 covered by a covering layer 32.

In the example, the tubular body has a cylindrical shape. Alternatively, different sections of the tubular body 22 transverse to the central axis A-A' have different diameters. For example, the tubular body 22 has a conical or other shape.

The frame 30 is for example formed from at least one elastic wire, for example from shape memory metal, such as Nitinol, or from polymer. The or each wire is for example configured in a zigzag or as a mesh defining cells.

The covering layer 32 closes off intermediate openings defined between the wire segments. It sealably defines the central passage 24 over the entire length of the body 22, with the exception of the aperture 26.

The covering layer 32 is for example formed based on a liquid-tight film, for example having a thickness smaller than 1 mm. The film is for example made from a silicone polymer, or from a fluorinated polymer like PTFE. In one example, the covering layer 32 is formed by a textile, for example weaved or knitted.

The central passage 24 is sealably defined by the peripheral wall 28. It opens axially on either side of the tubular body 22 through a proximal opening and a distal opening. It opens transversely through the aperture 26.

The aperture 26 leads into the inside of the central passage 24 and the outside of the tubular body 22.

In the first treatment device 10, the aperture 26 is a lateral aperture. The aperture 26 is arranged transversely in the peripheral wall 28 away from the proximal opening and distal opening of the tubular body 22.

The aperture 26 allows the insertion of the second implant 20.

Figure 3:
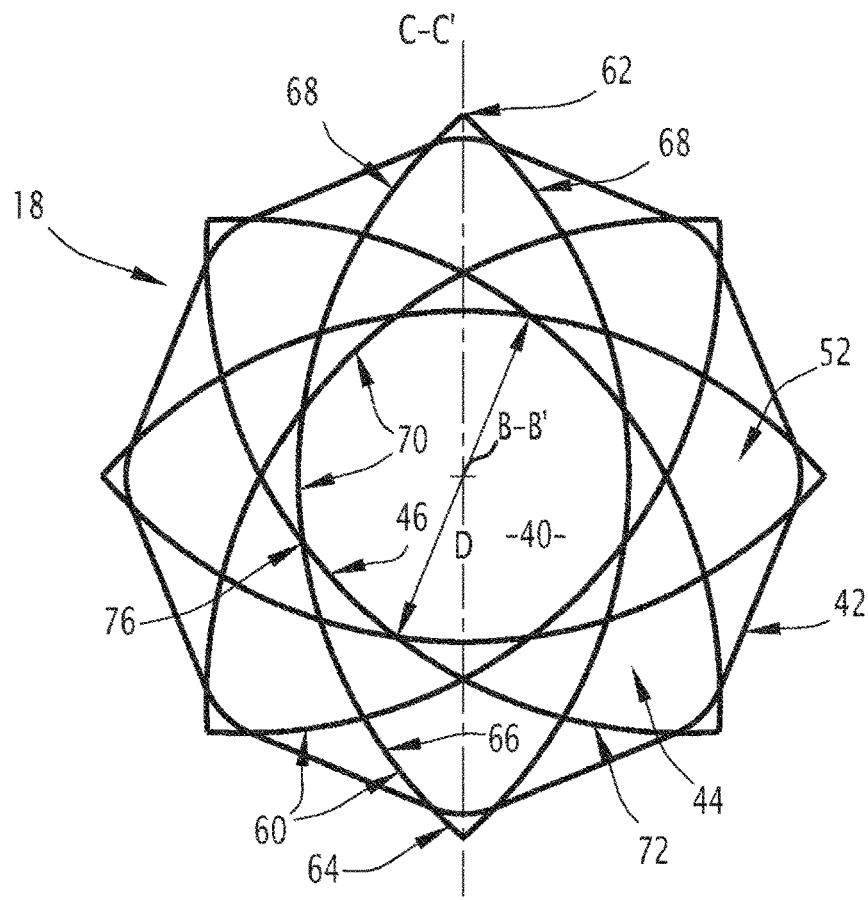
FIG. 3 is a top view of the elastic ring in a rest position.
Figure 4:
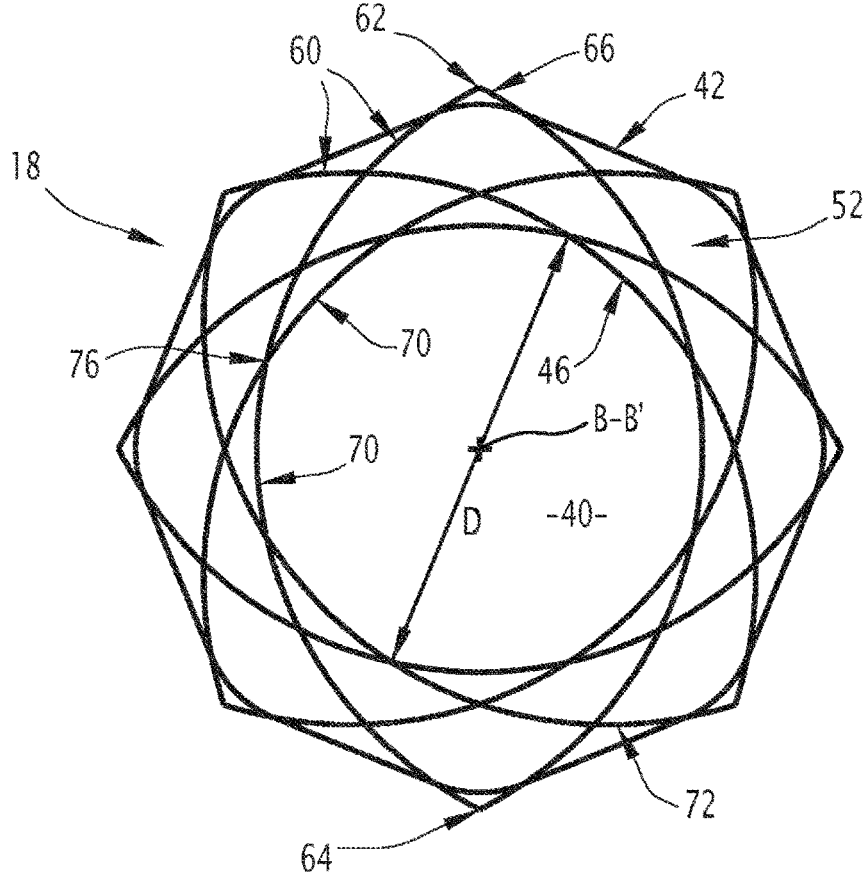
FIG. 4 is a top view of the elastic ring in an insertion position.

In reference to FIGS. 3 and 4, the elastic ring 18 defines an inner opening 40, an outer contour 42 and a bearing surface 44. The inner opening 40 is defined by a contour 46. The bearing surface 44 is defined between the outer contour 42 and the contour 46 of the inner opening 40. The bearing surface 44 is annular.

The elastic ring 18 is positioned on the tubular body 22 of the first implant 16 in the aperture 26.

In the first device 10, the ring 18 is attached on the tubular body 22 of the first implant 16 in the aperture 22. For example, the ring 18 is fixed to the tubular body 22 around the aperture 26 by fastening members (not shown). Advantageously, the fastening members are positioned on the outer contour 42 of the ring 18.

The ring 18 extends substantially circumferentially around a central axis B-B'. In the first device 10, the central axis B-B' of the elastic ring 18 is substantially perpendicular to the main axis A-A' of the first implant 16. Substantially perpendicular means that the axes form an angle relative to one another comprised between 85° and 95°.

The ring 18 has an inner face 50 intended to be facing the central passage 24 and an outer face 52 intended to be facing the outside of the first implant 16. The ring 18 is substantially flat.

The bearing surface 44 of the ring 18 has a slightly curved shape, substantially complementary to the peripheral wall 28 of the tubular body 22 around the aperture 26.

The elastic ring 18 comprises a covering layer covering the bearing surface 44 but not closing off the inner opening 40. The covering layer ensures the seal of the bearing surface 44 between the inner face 50 and the outer face 52. The covering layer is for example positioned on the outer face 52 of the elastic ring 18. Alternatively, the covering layer is positioned on the inner face 50 of the elastic ring 18.

The elastic ring 18 is advantageously radiopaque. This makes it possible to verify the orientation relative to the axis of the primary segment 12 of the aperture 26 in which the elastic ring 18 is positioned and to facilitate the placement in front of the branch 14.

The outer contour 42 is made up of at least one wire segment, here a series of wire segments. The outer contour 42 has the shape of a regular polygon, inscribed in a circle, the central axis B-B' passing through the center of the circle. When the ring 18 is in the treatment device 10, the shape of the outer contour 42 is for example maintained by the points of attachment to the first implant 16.

The diameter of the outer contour 42 is defined as the maximum distance between two points of the outer contour 42.

The diameter D of the inner opening 40 is defined as the maximum distance between two points of the contour 46 of the inner opening 40.

The ring 18 is deformable between a rest position and an insertion position, in which the inner opening 40 has a diameter larger than its diameter in the rest position. The ring 18 is shown in the rest position in FIG. 3 and in the insertion position in FIG. 4.

The ring 18 is elastically biased toward the rest position.

The deformation of the elastic ring 18 is an elastic deformation allowing a reversible increase of at least 20%, advantageously of at least 30% of the diameter of the inner opening 40.

Figure 5:
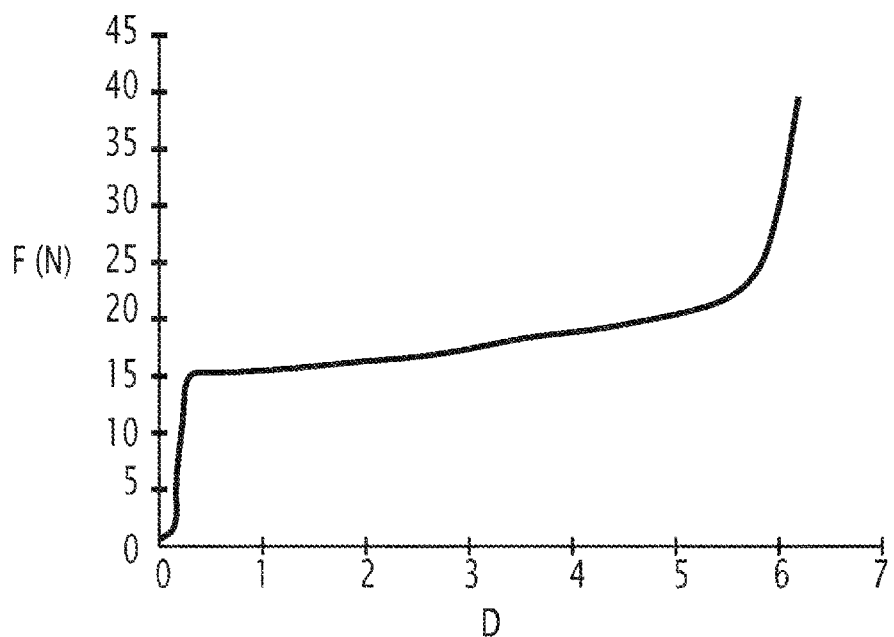
FIG. 5 is a graph of the force produced by the ring as a function of the diameter increase of the inner opening of the ring.

When a spreading force is exerted on the inner opening 40, the elastic ring 18 exerts an opposed resistance force F visible in FIG. 5. The larger the diameter D of the inner opening 40 is relative to the diameter of the inner opening 40 in the rest position, the larger the resistance force is. The resistance force is compensated by a reduction in the diameter of the outer contour 42, as described hereinafter. Indeed, the diameter of the outer contour 42 decreases when the resistance force increases.

The reversible deformation of the elastic ring 18 in particular results from the presence of strands 60 capable of spacing apart.

The elastic ring 18 comprises at least three strands 60 passing through the elastic ring 18.

Each strand 60 comprises a first end 62 and a second end 64 that are positioned on the outer contour 42. For example, the ends 62, 64 are engaged on the outer contour 42.

Advantageously, the ring 18 comprises at least one pair 66 of strands 60 comprising two paired strands 68. The paired strands 68 are strands 60 having shared ends, in particular their first end 62 and their second end 64.

Advantageously, the ring 18 comprises an even number of strands 60, the strands 60 being paired two by two.

In the example illustrated in FIGS. 1 to 4, the elastic ring 18 comprises eight strands 60 paired two by two. Thus, the elastic ring 18 of the example comprises 4 pairs 66 of paired strands 68.

Each strand 60 is extended between the first end 62 and the second end 64.

Each strand 60 has a diameter comprised between 0.1 mm and 2 mm, for example of 0.2 mm.

In the illustrated example, the strands 60 all have the same length.

The strand 60 is made from an elastic wire. For example, the wire is made from shape memory metal, such as Nitinol. Alternatively, the wire is made of polymer.

Each strand 60 has an elasticity modulus, for example, comprised between 20 GPa and 200 GPa. The elasticity of the strand 60 constrains the strand 60 toward a taut configuration in which the strand 60 is slightly curved between the first end 62 and the second end 64.

The only intersections between two strands 68 of a pair 66 are at their ends 62, 64. The pair 66 of strands 68 defines an axis C-C' passing through the first end 62 and the second end 64 of the paired strands 68.

In the example, the ends 62, 64 of the strand 60 are retained by the outer contour 42; each strand 60 therefore has a deflection between its ends 62, 64. Each strand 60 thus has a curved shape.

Thus, a pair 66 of strands 68 has an oblong shape, in particular an eye shape. An eye shape means that each paired strand 68 is substantially in the shape of an arc of circle, the curvatures of the arcs of circle being opposite.

The oblong shape is advantageously symmetrical relative to the axis C-C' of the pair 66 of strands 68.

The strands 60 pass through the ring 18. This means that the angle between the angular position of the first end 62 and the angular position of the second end 64 of a strand 60, relative to the central axis B-B' of the ring 18, is equal to 180°.

Advantageously, the first end 62 and the second end 64 of each strand 60 are substantially diametrically opposite relative to the central axis B-B'.

The axis C-C' of the pair 66 of strands 68 advantageously passes through the central axis B-B' of the ring 18.

The ends of the pairs 66 of strands 60 are distributed angularly on the outer contour 42. This makes it possible to distribute all of the forces around the outer contour 42.

The strands 60 extend substantially in a single plane.

The inner opening 40 is a central passage opening into the inner face 50 and into the outer face 52 of the ring 18.

As previously described, the inner opening 40 has a variable diameter.

When the ring is in the insertion position, the diameter of the inner opening 40 is greater than or equal to the diameter of the second implant 20 to allow its insertion. For example, the diameter of the inner opening 40 in the insertion position is greater than 4 mm and advantageously comprised between 4 mm and 10 mm.

In the rest position, the diameter of the inner opening 40 is strictly smaller than the diameter of the second implant 20.

For example, the diameter of the inner opening 40 in the insertion position is smaller than 10 mm and advantageously comprised between 4 mm and 8 mm.

The width of the bearing surface 44 is the difference between the diameter of the outer contour 42 and the diameter of the inner opening 40. The width of the bearing surface 44 is preferably comprised between 30% and 60% of the diameter of the inner opening 40 in the rest position.

The contour 46 of the inner opening 40 is capable of conforming to the outer contour 42 of the second implant 20.

The contour 46 of the inner opening 40 is defined by a portion 70 of each strand 60. The contour 46 of the inner opening 40 has a pseudo-polygonal shape. "Pseudo-polygonal" refers to a substantially planar closed figure delimited by several segments connected by vertexes. For example, the segments are substantially curved between the vertexes of the pseudo-polygon.

The vertexes of the pseudo-polygon are situated at intersections between two strands 60. In particular, the vertexes are situated at intersections between strands 60 not belonging to the same pair 66.

The vertexes of the pseudo-polygon are positioned regularly around the central axis B-B'. Thus, the vertexes are inscribed in a circle with a center passing through the axis B-B'.

Advantageously, the vertexes of the pseudo-polygon are substantially in the same plane.

Furthermore, the intersections between the strands 60 that are situated between the outer contour 42 and the inner opening 40 define the bearing surface 44, on which the second implant 20 rests once implanted in the aperture 26. This bearing surface 44 has an area greater than 80% of the area of the inner opening.

Advantageously, the strands 60 are formed from a single wire 72. Advantageously, the wire 72 is also used to form the outer contour 42.

The wire 72 is preferably braided, to form junctions between the strands 60. The junctions serve to distribute the stresses between the strands 60.

Figure 6:
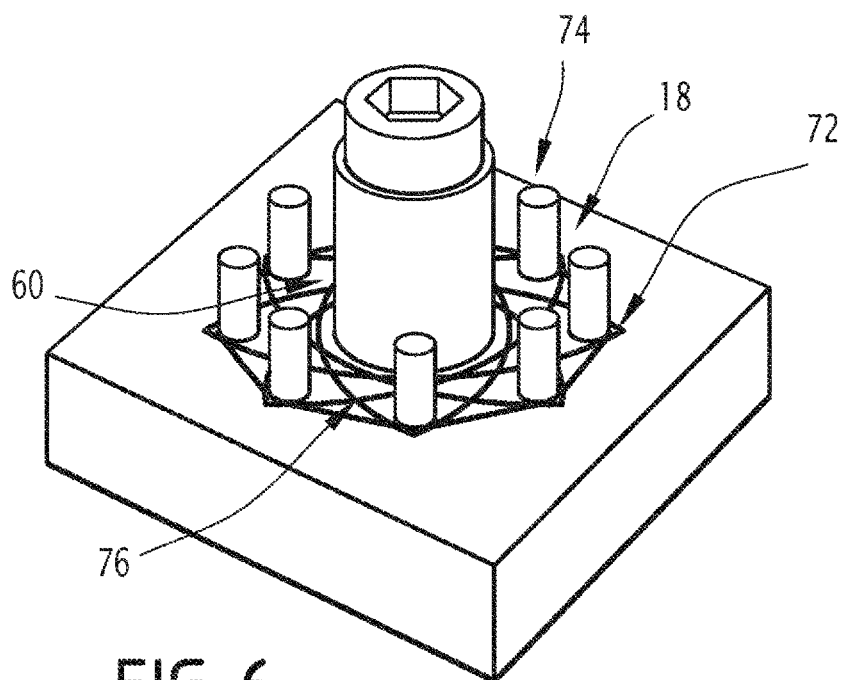
FIG. 6 is a schematic view of an assembly for manufacturing the elastic ring.

FIG. 6 shows an assembly for manufacturing the elastic ring making it possible to braid the wire 72.

During this braiding, the wire 72 is placed by following a path between studs 74 that make possible to position the different intersections between the strands 60 of the wire 72.

At each intersection, the wire 72 passes below or above the met wire strand 72. The braiding consists of alternating between a passage of the wire 72 below the met strand of wire 72 and a passage of the wire 72 above the met strand 60 of wire 72 between two successive intersections 76, followed by the development of a portion of the outer contour 42 to reach another end of two paired strands 60.

The elastic ring 18 thus formed therefore has a maximum thickness substantially equal to twice the diameter of the wire 72, due to intersections 76 where several strands 60 overlap.

For example, when the ring 18 is formed by braiding, the intersections 76 make it possible to define the ends of each strand 60 on the outer contour 42 and the vertexes of the pseudo-polygon.

The ring 18 is thus a flat braid having an extensible inner opening 40.

The nature of the wire 72 of the strands 60 makes it possible to keep the shaping of the optimal ring. For example, for the implantation of the device, the ring 18 is folded into a release device of the first implant 16 and recovers the optimal initial shape thereof after deployment.

As illustrated by FIGS. 1 and 2, the second implant 20 comprises a second tubular body 80 around a central primary axis D-D'. The central primary axis D-D' is substantially parallel to the central axis B-B' of the ring 18.

The second tubular body 80 comprises a peripheral wall 82 defining an auxiliary central passage 84. When the second implant 20 is inserted into the central opening 40, the auxiliary central passage 84 opens into the central passage 24 of the first implant 16.

Like for the peripheral wall 28 of the tubular body 22, the wall 82 of the second body 80 comprises an open-cell frame covered by a covering layer. For example, the covering layer of the second tubular body 80 is made from the same material as the covering layer 32 of the first body 22. The frame is for example formed by at least one wire configured in a zigzag, or by a mesh of wires defining cells.

As illustrated in FIG. 2, the second implant 20 comprises a stop 88. For example, the stop 88 comprises a flange protruding radially relative to the primary central axis D-D' of the second tubular body 80, advantageously perpendicular to the primary central axis D-D'. The flange is for example continuous over the entire periphery of the distal edge around the primary central axis D-D'. Alternatively, the flange is formed by a plurality of discontinuous disjointed fingers. Once the second implant 20 is mounted on the first implant 16, the stop 88 is applied against the annular bearing surface 44 and optionally against an inner surface of the first tubular body 22 situated around the aperture 26 to prevent the outward radial movement of the second implant 20 with respect to the first implant 16. The second implant 20 thus has a general T-shape and is designated by the term "T-stent".

The annular bearing surface 44 being wide and two-dimensional, it gives the stop 88 robust support.

The second implant 20 is deformable between a retracted insertion configuration and a deployed configuration implanted in the branch 14 and in the aperture 26 of the first implant 16, as shown in FIG. 2. Advantageously, the second implant 20 is auto-expandable.

In the retracted configuration, the second implant 20 has a minimal radial extent. In this configuration, the stop is radially contracted near the axis D'-D'. The second implant 20 is able to be conveyed through the central passage 24 and the aperture 26 and to be inserted into the inner opening 40 of the elastic ring 18. In the deployed configuration shown in FIG. 2, the second tubular body has a maximal radial extent around the axis D-D'. The stop 88 is deployed transversely relative to the axis D-D'.

In one example, the second implant 20 is maintained in a launcher in the retracted configuration, when the ring 18 is in the insertion configuration, the diameter of the inner opening 40 is greater than or equal to the diameter of the launcher of the second implant 20.

To guarantee a good seal, the outer contour of the second implant 20 in its deployed configuration has an extent greater than the extent of the inner opening 40 of the ring 18 in the rest position. The deployed second implant 20 has, in its deployed configuration, an outer diameter greater than the diameter of the inner opening 40 of the ring 18 in rest position.

When the second implant 20 is inserted into the inner opening 40, the ring 18 is elastically deformed around the second tubular body 80. The contour 46 of the inner opening 40 then has a shape conjugated to the outer contour of the second body 80 in contact with the elastic ring 18.

When the second implant 20 is received in the inner opening 40, a radial retaining and sealing force applies against the outer surface of the second tubular body 80, irrespective of the spatial configuration of the second tubular body 80 relative to the first tubular body 22. In particular, the seal is produced over the entire contour 46 of the inner opening 40, by each of portions 70 of the strands 60 defining the central pseudo-polygon.

The elastic ring 18 therefore guarantees a seal generating a significant force at the interface between the first implant 16 and the second implant 20 in the aperture 26. Furthermore, the distribution of portions 70 of the strands 60 is adapted so that the ring 18 has a uniform force over the second implant 20, all along the contour 46 of the inner opening 40.

Furthermore, the second implant 20 is retained robustly in the first implant 16. The force necessary to pull the second implant 20 out from the elastic ring 18 is for example greater than 10 N.

In particular, the elasticity of the ring 18 allows an adaptation of the inner opening 40 in case of shrinkage of the diameter of the second implant 20 (also called recoil). The treatment device therefore makes it possible to maintain a continuous and active pressure on the second implant in the branch 14.

The device 10 is able to adapt to the relative movements and deformations between the first implant 16 and the second implant 20, for example imposed by the systolic-diastolic flow in the artery 12. Indeed, the device 10 can move during the systolic-diastolic flow, while the second implant in the collateral branch 14 is stationary. There is thus a continuous adaptation of the seal during these micro-movements between the second implant 20 and the ring 18 that continuously constrains the auto-expanding second implant 20, which is continuously constrained toward the equilibrium position thereof.

In one example, the diameter of the inner opening 40, called D, of the elastic ring 18 at rest and the diameter of the outer contour 42, called $D_{ext}$, are parameters determined, before implantation, from the diameter of the first implant 16, called $D_1$, and the diameter of the second implant 20, called $D_2$.

Advantageously, to obtain an optimal connection between the second implant 20 and the ring 18, it is desired that $D=2/3\ D_2$.

The diameter of the outer contour $D_{ext}$ is defined as a function of the diameter of the inner opening 40 according to the following equation: $D_{ext}=4/3*D*x$, where x is a factor dependent on the bearing surface 44.

Furthermore, to obtain a penetration of the second implant 20 into the first implant 10 equal to 10% of the diameter $D_1$ of the first implant 16, it is advantageous for the diameter $D_{ext}$ of the outer contour 42 of the ring 18 to be equal to 20% of the outer perimeter of the first implant 16.

This means that it is preferable that $D_{ext}=0.2\ \pi D_1$.

Thus, with these conditions, the factor x dependent on the bearing surface can be deduced from the following equation:

$$x=0.2\ \pi*8/9*D_1/D_2.$$

A second device (not shown) will now be described. Unlike the first device 10, the tubular body 22 of the first implant 16 comprises a mesh made up of at least one wire, the elastic ring 18 being formed on the tubular body of the first implant in the aperture using at least one wire 72 of the mesh. In this second device, the elastic ring 18 is directly braided with the wires 72 of the first implant 16. In this device, the elastic ring 18 is integral with the frame 30 of the first implant 18. This improves the resistance of the device.

In a third treatment device, the aperture 26 is positioned in the axis A-A' of the tubular body 22. The central axis B-B' of the ring 18 is then substantially collinear to the axis A-A' of the tubular body 22. Unlike the first device 10, the first implant 16 defines an axial aperture 26 in which a second implant 20 is inserted.

The axial aperture 26 is for example defined at the distal opening of the tubular body 22. Alternatively, the aperture 26 is defined at the proximal opening of the tubular body 22.

The first implant 16 comprises an elastic ring 18 extending in the axial aperture. The bearing surface 44 of the ring 18 extends transversely to the axis A-A' at the level of the aperture 26.

The third device is for example used to join two consecutive implants 16, 20. Indeed, the axes A-A' of the first implant and of the second implant 20 are substantially collinear. The two central passages 24, 84 communicate with no elbow.

In the third device, the second implant is axially movable in the first implant 16, and retained sealably by an elastic ring 18. This allows the operator to adjust the relative axial position of the implants with respect to one another, to adapt to different anatomical conformations.

In one alternative, the elastic ring 18 can be used with no second implant 20, for example to reduce the fluid passage flow rate in the primary conduit 12. The ring 18, due to its elastic properties, adapts to the movements imposed by the flow of liquid circulating in the first implant 16.

In the example, eight strands are shown. However, the number of strands can be different as long as there are at least three strands 60, preferably at least four strands 60, to define the contour 46 of the inner opening 40 of the ring 18.

The number of pairs 66 of strands 60 is advantageously comprised between 2 and 8.

Alternatively, the arrangement of the strands 60 is different. For example, the ends 62, 64 of the strands 60 on the outer contour 42 are different. For example, several strands 60 have different lengths.

In the example shown in FIG. 1, the first implant 16 is an endoprosthesis that comprises a covering layer 32. In one alternative, the first implant 16 is a stent that does not comprise a covering layer 32 on the frame 30.

Alternatively, the body 22 on which the ring 18 is positioned is not tubular.

The invention claimed is:

1. A treatment device comprising:
    a first piece comprising a first tubular implant having a side aperture; and
    a second piece, distinct from the first piece, the second piece comprising an elastic ring, disposed in the side aperture of the first piece, the elastic ring defining an inner opening, an outer contour and an annular bearing surface between the inner opening and the outer contour, the ring being deformable between a rest position and an insertion position, in which the inner opening has a diameter greater than its diameter in the rest position, the ring being elastically biased towards the rest position,
    wherein the ring comprises at least three strands passing through the ring, each strand comprising a first end and a second end, each positioned on the outer contour, the contour of the inner opening being defined by a portion of each strand and having a pseudo-polygonal shape.

2. The treatment device according to claim 1, wherein the strands are formed from a single wire.

3. The elastic ring according to claim 2, wherein the single wire is braided.

4. The treatment device according to claim 1, wherein the strands extend in a single plane.

5. The treatment device according to claim 1, wherein the width of the bearing surface is comprised between 30% and 60% of the diameter of the inner opening in the rest position.

6. The treatment device according to claim 1, the elastic ring comprising at least one pair of strands, each pair of strands comprising a first strand and a second strand, the first and second strands connected to one another at respective first and second ends.

7. The treatment device according to claim 6, wherein the paired strands define an oblong shape.

8. The treatment device according to claim 6, wherein the ends of the pairs of strands are distributed on the outer contour.

9. The treatment device according to claim 6, the elastic ring comprising an even number of strands, the strands being paired two by two.

10. The elastic ring according to claim 6, wherein the paired strands define an eye shape.

11. The elastic ring according to claim 6, comprising eight strands.

12. The treatment device according to claim 1, wherein the deformation of the ring is an elastic deformation allowing a reversible increase of at least 20% of the diameter of the inner opening.

13. The treatment device according to claim 1, wherein each strand has a diameter comprised between 0.1 mm and 2 mm.

14. The treatment device according to claim 1, wherein the elastic ring is positioned on a body of the first implant in the aperture, the inner opening defining the insertion passage of a second implant.

15. The treatment device according to claim 14, wherein the body is made up of a mesh of at least one wire, the ring being formed on the body of the first implant in the aperture using at least one wire of the mesh.

16. The treatment device according to claim 14, wherein the ring is attached on the body of the first implant in the aperture.

17. The treatment device according to claim 14, wherein the aperture is positioned on the wall of the body.

18. The treatment device according to claim 14, wherein the aperture is positioned in the axis of the body.

19. The treatment device according to claim 14, wherein the body is tubular.

20. The elastic ring according to claim 1, wherein the deformation of the ring is an elastic deformation allowing a reversible increase of at least 30% of the diameter of the inner opening.

* * * * *